(12) United States Patent
Whittacre et al.

(10) Patent No.: US 11,672,901 B2
(45) Date of Patent: Jun. 13, 2023

(54) RADIOPHARMACEUTICAL PIG CLEANING AND TRANSPORTATION SYSTEM

(71) Applicant: ec2 Software Solutions, LLC, Las Vegas, NV (US)

(72) Inventors: Bretten Hug Whittacre, Henderson, NV (US); Jared Mark Johnson, Henderson, NV (US)

( * ) Notice: Subject to any disclaimer, the term of this patent is extended or adjusted under 35 U.S.C. 154(b) by 62 days.

(21) Appl. No.: 17/303,712

(22) Filed: Jun. 4, 2021

(65) Prior Publication Data
US 2022/0387699 A1    Dec. 8, 2022

(51) Int. Cl.
*A61M 5/00* (2006.01)
*B08B 1/00* (2006.01)
*B08B 1/04* (2006.01)

(52) U.S. Cl.
CPC ............ *A61M 5/001* (2013.01); *B08B 1/006* (2013.01); *B08B 1/04* (2013.01)

(58) Field of Classification Search
None
See application file for complete search history.

(56) References Cited

U.S. PATENT DOCUMENTS

| | | |
|---|---|---|
| 6,576,918 B1 | 6/2003 | Fu |
| 6,722,499 B2 | 4/2004 | Reich |
| 6,820,660 B1 | 11/2004 | Ludwig |
| 7,086,133 B2 | 8/2006 | Reich |
| 7,268,359 B2 | 9/2007 | Fu |
| 9,646,730 B2 | 5/2017 | Prosser |
| 2003/0146399 A1 | 8/2003 | Martin |
| 2005/0234424 A1 | 10/2005 | Besing |
| 2008/0210892 A1 | 9/2008 | Wagner |
| 2010/0084585 A1 | 4/2010 | Prosser |
| 2013/0266487 A1 | 10/2013 | Osborn |
| 2019/0348187 A1 | 11/2019 | Kamen |

OTHER PUBLICATIONS

Written Opinion of of the International Searching Authority for PCT application PCT/US2021/072123 dated Mar. 9, 2022, 5 pages.

*Primary Examiner* — Eric W Golightly
(74) *Attorney, Agent, or Firm* — Law Office of Jenna F. Karadbil, P.C.; Juan P. Rodriguez

(57) ABSTRACT

A pig cleaning and transportation system is disclosed. Exemplary implementations include a platform with a plurality of apertures; a plurality of securing mechanisms, each mechanism within each aperture and configured to hold a pig and allow it to rotate around its longitudinal axis; a base underneath the platform; and a cleaning element connected to the base and positioned on each longitudinal side of the platform in pressure contact with the pigs on the plurality of securing mechanisms, each cleaning element including at least one cleaning material surface.

15 Claims, 14 Drawing Sheets

RADIOPHARMACEUTICAL PIG CLEANING AND TRANSPORTATION SYSTEM

FIELD OF THE DISCLOSURE

The present disclosure relates to a radiopharmaceutical pig cleaning and transportation system.

BACKGROUND

A radiopharmaceutical pig is a device used to transport a syringe containing a radiopharmaceutical medication. Given the radioactive nature of the radiopharmaceutical medication, such pigs are required in order to safely transport medications during various stages of preparation, transportation, and storage. Most pigs are made of two interlocking components and are composed of some base shielding element. In most, but not all, cases lead is used. This ensures that these radiopharmaceutical syringes are safely transported for use on the patient without any adverse effects to pharmaceutical or medical staff.

Pigs are sturdy enough to warrant their sanitization and re-use. Various government guidelines (such as those found under the United States Pharmacopeial Convention regulation USP-825) require that pigs a) should be disinfected within a minimum 70% by volume USP grade isopropanol (IPA) solution or equivalent disinfectant, b) should be sterilized within a minimum International Sterilization Organization level 5 environment, and c) should be stored to maintain required sterility as they travel thru various environments (including primary engineering control sections, cleanrooms, buffer-rooms, etc.). Many other methods of sanitation and re-use fail to provide for the efficient sanitation of multiple pigs at the same time in order to speed up post-use storage and transport. Furthermore, additional systems are currently required to effectively store disinfected pigs prior to re-use between various areas and multiple levels of sanitation.

This background information is provided to reveal information believed by the applicant to be of possible relevance to the present invention. No admission is necessarily intended, nor should be construed, that any of the preceding information constitutes prior art against the present invention.

SUMMARY

One aspect of the present disclosure relates to a pig cleaning and transportation system. The system may include a platform with a plurality of apertures, a plurality of securing mechanisms, a base underneath the platform, and a cleaning element connected to the base and positioned on each longitudinal side of the platform in pressure contact with the pigs on the plurality of securing mechanisms. Each securing mechanism may be positioned within each aperture and configured to hold a pig and allow it to rotate around its longitudinal axis. Furthermore, each cleaning element may include at least one cleaning material surface.

In some implementations of the system, the platform may further include a handle.

In some implementations of the system, each securing mechanism may further include a plurality of axes, each axis fitted within each aperture and configured to pressure-fit the interior of a pig, each axis further including at least one O-ring, the O-ring configured to pressure-fit between the axis and the inside of the pig.

In some implementations of the system, the cleaning element may further include at least one roller and at least one cleaning material dispensing container, the at least one roller and dispensing container configured to dispense a cleaning material across the cleaning surface.

In some implementations of the system, the cleaning element may further include a sponge, the sponge configured to be in pressure contact with the plurality of pigs on the platform.

In some implementations of the system, the system may further include a top cleaning element, the top cleaning element including an axis connected to at least one of the other cleaning elements of the system.

In some implementations of the system, the top cleaning element may further include at least one roller and at least one cleaning material dispensing container. The at least one roller may be configured to be in pressure contact with the top of the plurality of pigs. Furthermore, the at least one roller and dispensing container may be configured to dispense a cleaning material across the cleaning surface.

In some implementations of the system, the top cleaning element may further include a sponge. The sponge may be configured to be in pressure contact with the plurality of pigs on the platform.

In some implementations of the system, the system may further include a cover configured to lock with the platform.

In some implementations of the system, the bottom of the platform may be configured to fit with the top of the cover.

Another aspect of the present disclosure relates to a method of cleaning and transporting a plurality of pigs utilizing a system comprising a platform with a plurality of apertures; a plurality of securing mechanisms, each mechanism within each aperture, and configured to hold a pig and allow it to rotate around its longitudinal axis; a base underneath the platform; and a cleaning element connected to the base and positioned on each longitudinal side of the platform in pressure contact with the pigs on the plurality of securing mechanisms, each cleaning element including at least one cleaning material surface. The method may include placing at least one pig in contact with the platform by way of one of the securing mechanisms; and moving the platform along the base such that the at least one pig is rotating with the securing mechanism and in pressure contact with the cleaning material surface.

These and other features, and characteristics of the present technology, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

BRIEF DESCRIPTION OF THE DRAWINGS

The details of the present disclosure, both as to its structure and operation, can best be understood by referring to the accompanying drawings, in which like reference numbers and designations refer to like elements.

DETAILED DESCRIPTION

Figure 1:
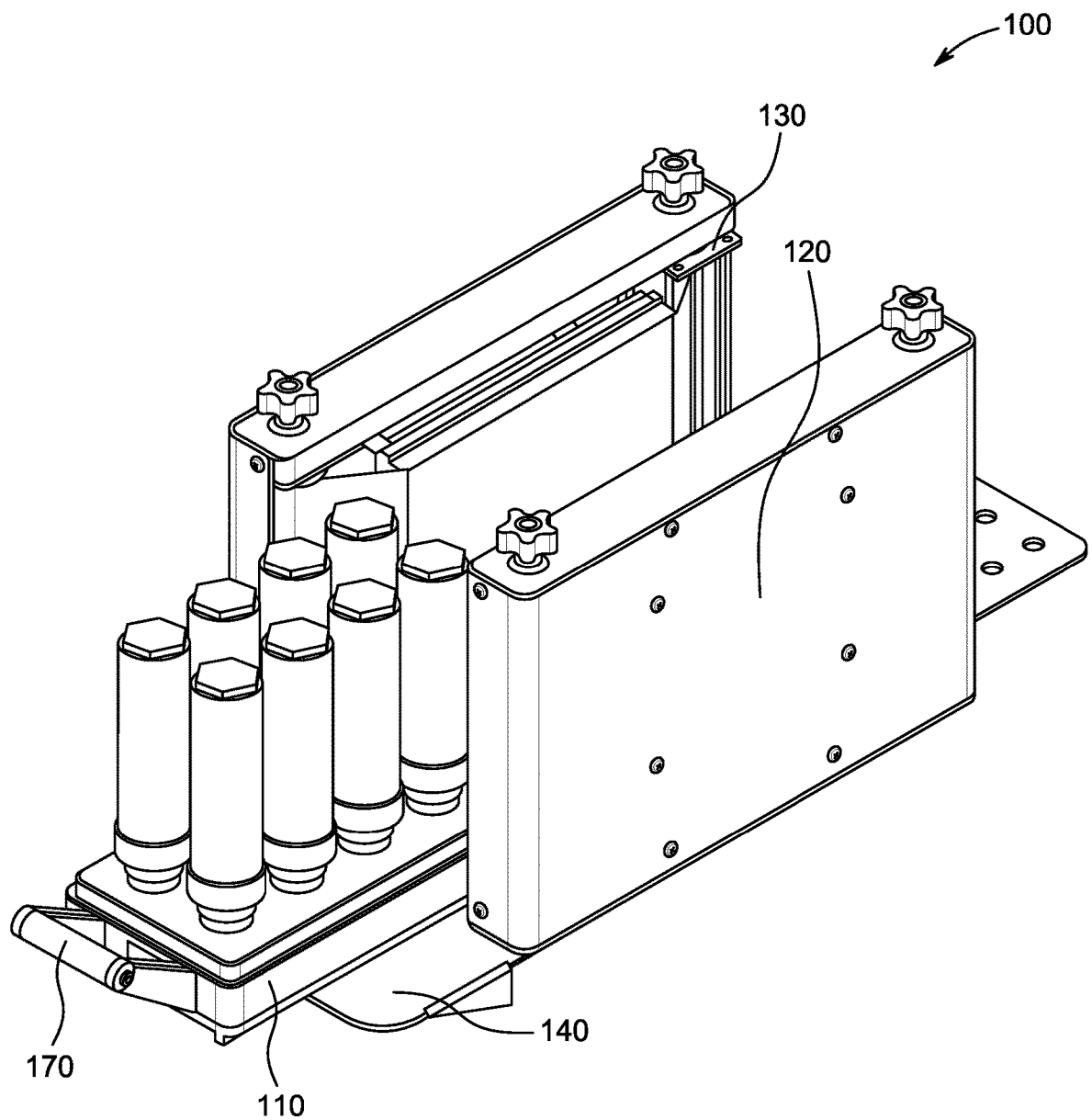
FIG. 1 illustrates an exemplary angled overall view of a pig cleaning and transportation system 100, in accordance with one or more embodiments.
Figure 2:
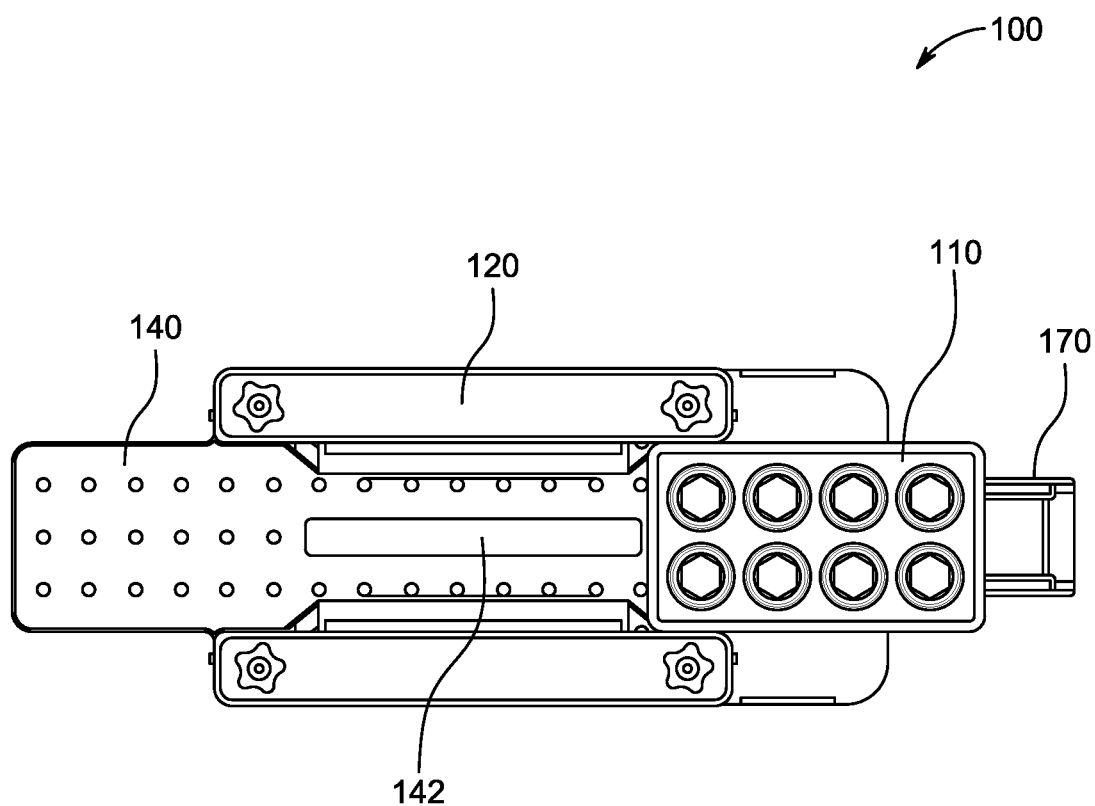
FIG. 2 illustrates an exemplary top view of the pig cleaning and transportation system 100, in accordance with one or more embodiments.
Figure 3:
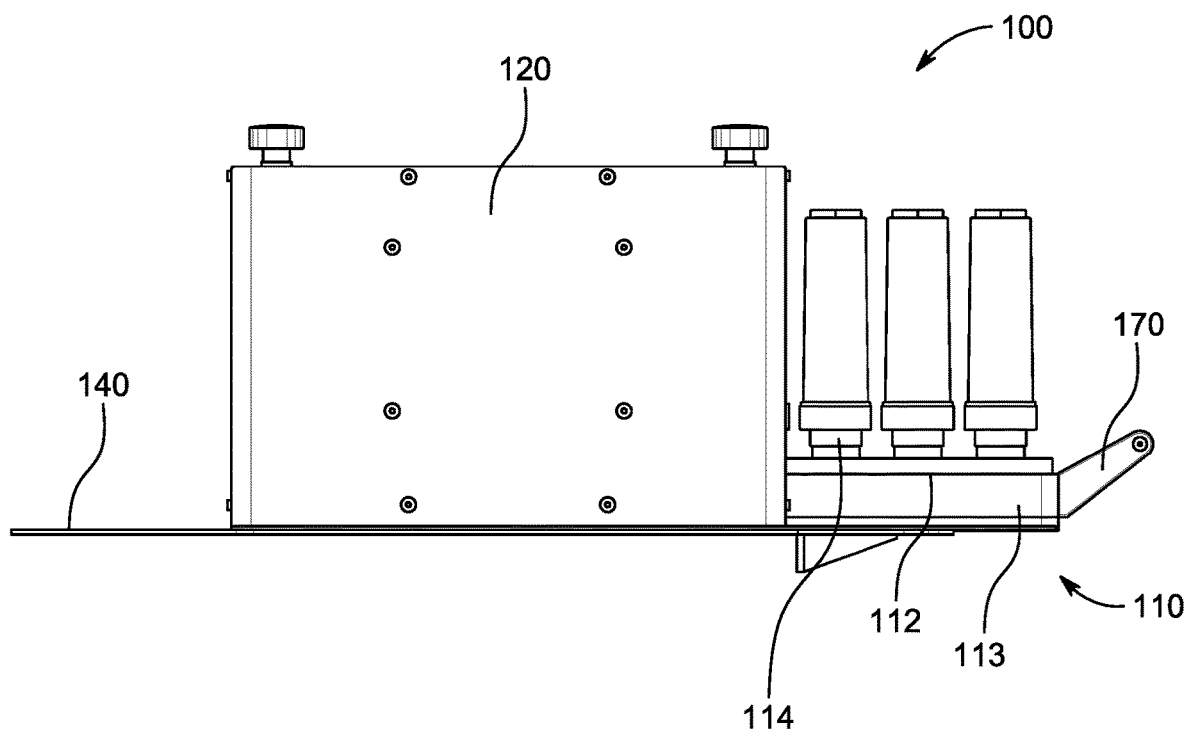
FIG. 3 illustrates an exemplary side view of the pig cleaning and transportation system 100, in accordance with one or more embodiments.

FIG. 1 illustrates an exemplary angled overall view of a pig cleaning and transportation system 100. Additionally, FIG. 2 illustrates an exemplary top view and FIG. 3 illustrates an exemplary side view of the pig cleaning and transportation system 100. The system 100 as shown in the figures includes a platform 110 with a plurality of apertures 111, a plurality of securing mechanisms 114, a base 140 underneath the platform 110, and a cleaning element 120 connected to the base 140 and positioned on each longitudinal side of the platform 110 in pressure contact with the pigs on the plurality of securing mechanisms 114. Each securing mechanism 114 may be positioned within each aperture 111 and is configured to hold a pig and allow it to rotate around its longitudinal axis. Furthermore, each cleaning element 120 may include at least one cleaning material pressure surface 126. The system 100 may be sized and scaled to fit within a primary engineering control (PEC) device or room that provides the required amount of sanitation (such as the ISO level 5 sanitation required under USP-825) for the cleaning of the pigs. Examples of such PEC devices may include hoods such as laminar airflow workbenches (also known as LAFWs or "horizontal hoods"), biological safety cabinets (also known as BSCs or "vertical hoods") and compounding aseptic isolators (also known as CAIs or "glove boxes").

The platform 110 is one of the principle structural components of the system 100, along with the base 140, that carries a plurality of pigs thru the system 100. The platform 110 is supported by the base 140 and may include a plurality of apertures 111. The apertures 111 are used to retain structural communication between the platform 110 and the securing mechanisms 114. Other embodiments of the system 100 may omit the apertures 111 if there is another method of structurally holding the securing mechanisms 114 to the platform 110. For example, the securing mechanisms 114 may be magnetically attached to the platform 110. The plurality of apertures 111 may include any non-zero number of apertures 111 and can be aligned in any configuration that will allow for sufficient pressure contact between the pigs on the securing mechanisms 114 and the cleaning material pressure surface 126. The platform 110 may be composed of any material that may allow for sufficient structural stability during the pig cleaning and transportation process. This may include metal, glass, plastics, resins, or any composite thereof.

A plurality of securing mechanisms 114 are in structural communication with the platform 110. Each securing mechanism 114 is meant to secure a pig in place and rotate said pig along its longitudinal axis in order to place the pig in pressure contact with the cleaning material pressure surface 126. In the first embodiment, as shown in many of the figures, the securing mechanism 114 may be shaped to the interior of pig and hold the pig in place thru pressure contact. Additional embodiments of the system 100 may include securing mechanisms 114 that hold the pigs in place thru other mechanisms including compatible screw threads, magnets, clips, grips, non-reactive adhesives, or any such methods that would allow for the appropriate hold, spacing, and rotation of pigs on top of the platform 110. Each securing mechanism 114 may be composed of similar material to that of the platform 110 or any compatible material that would allow for the securing and rotation of the pigs with the system 100 during either the cleaning or transportation process. Every securing mechanism 114 may also include an internal cleaning mechanism 109 that will aid in the sanitation of each pig's interior cavity during the sanitation process. An internal cleaning mechanism 109 may include brush bristles, smaller fitted sections of cleaning material 128 (discussed further in the specification), UV light filaments, or any other potential device, system, or material that may be fitted to the interior cavity of each pig during the sanitation process.

A base 140 provides support for the side cleaning elements 120 and is configured to allow for the movement of the platform 110 along the length of the base 140. The base may be wide enough so that the cleaning elements 120 are connected along the edges of the base 140 and provide pressure contact between the cleaning material surface 126 and the plurality of pigs on the platform 110. As seen in the figures, the base 140 may simply include a structural surface that holds the cleaning elements 120 and allow for the frictionless movement of the platform 110. Other embodiments may include additional rolling or sliding elements so as to aid in the movement of the platform 110 along the base 140. The base 140 may also include at least one platform alignment rail 142 that will aid in the alignment of the platform 110 as it moves along the base 140. The alignment rail 142 also aids in maintaining consistent pressure contact between the pigs and the cleaning material surface 126 as well as assisting in the rotation of the pigs along the axis of each securing mechanism 114 during the sanitation process. Such an alignment rail can be along the middle of the base 140 between the securing mechanisms 114 or can correspond with either the inner or outer edges of the longitudinal cover guides 121 included in some embodiments of the platform 110. The base 140 may be composed of similar material to that of the platform 110 or any compatible material that would allow for the securing of the side cleaning elements 120 and supporting of the platform 110 during the pig cleaning process.

The system 100 also includes at least one side cleaning element 120 connected along at least one edge of the base 140. The first embodiment shown in the figures shows two side cleaning elements 120 along both sides of the base 140 in order to clean twice as many pigs simultaneously during the pig cleaning process. Each cleaning element 120 includes at least one cleaning material surface 126 that holds a cleaning material 128 against the outer surface of the pigs in order to facilitate cleaning of the pigs. The cleaning material 128 may be composed of any material commonly used for cleaning such as sponges, cloth, and/or paper products that will distribute cleaning solutions and/or compounds and clean the pigs within the system 100. Additional elements and embodiments of the side cleaning element 120 will be discussed along with FIGS. 9 through 13 in the specification. The side cleaning elements 120 may be composed of similar material to that of the platform 110 or of any compatible material that would allow for the cleaning of the pigs within the system 100.

The first embodiment of the system 100, as shown in the figures, also includes a handle 170 attached to the platform 110. The handle 170 aids in the movement of the platform 110 along the base 140 during the pig cleaning process as well as in the transportation of the platform 110 with the pigs during transportation either before or after cleaning. The handle 170 may be either structurally merged with the platform 110 or separate to detach from the platform 110 and allow better isolation of the platform 110 on the base 140. The handle 170 may be composed of similar material to that of the platform 110 or any compatible material that would allow for the movement of the platform 110 during the pig cleaning and transportation process.

Figure 4:
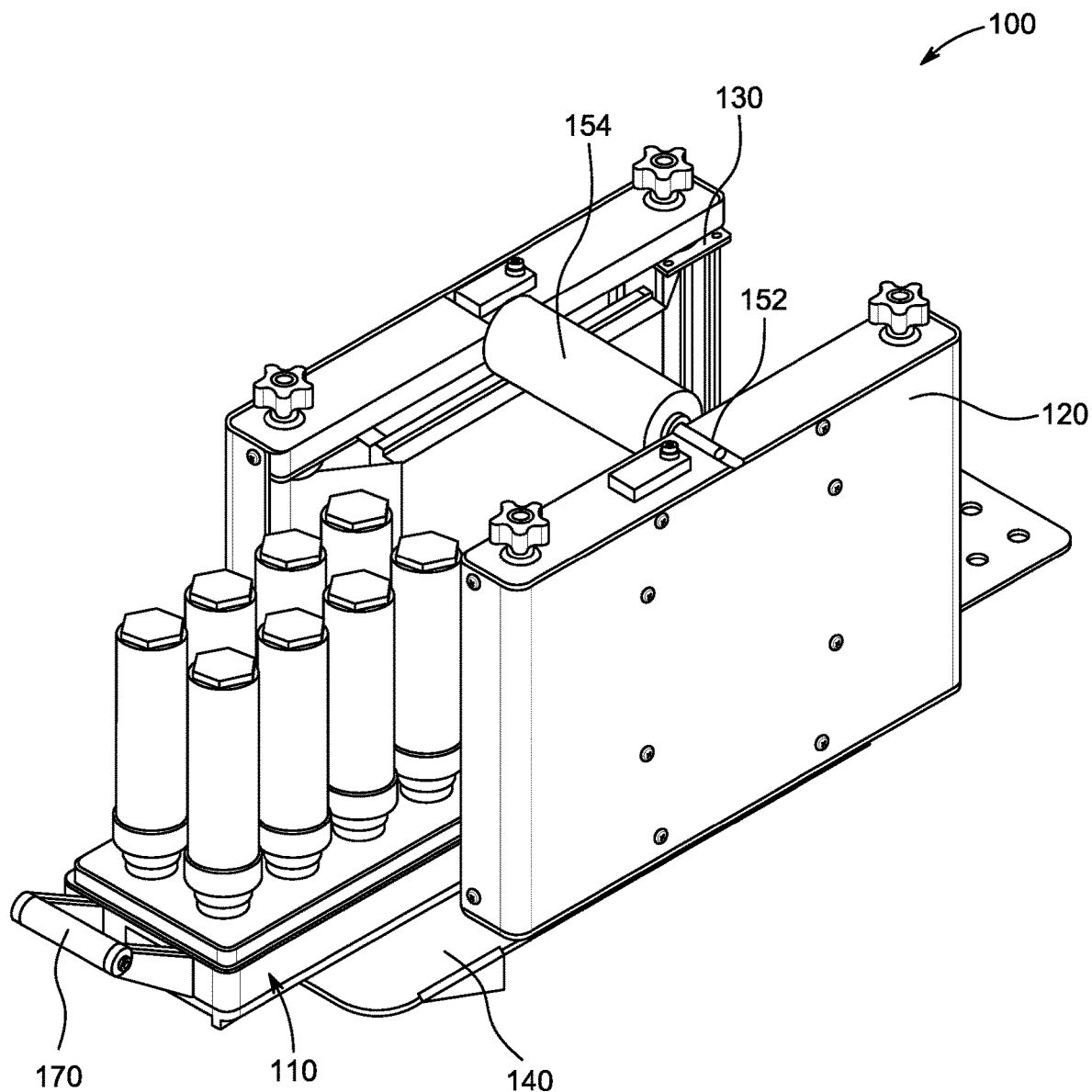
FIG. 4 illustrates an exemplary angled overall view of a second embodiment of the pig cleaning and transportation system 100 including a top cleaning element 150, in accordance with one or more embodiments.
Figure 5:
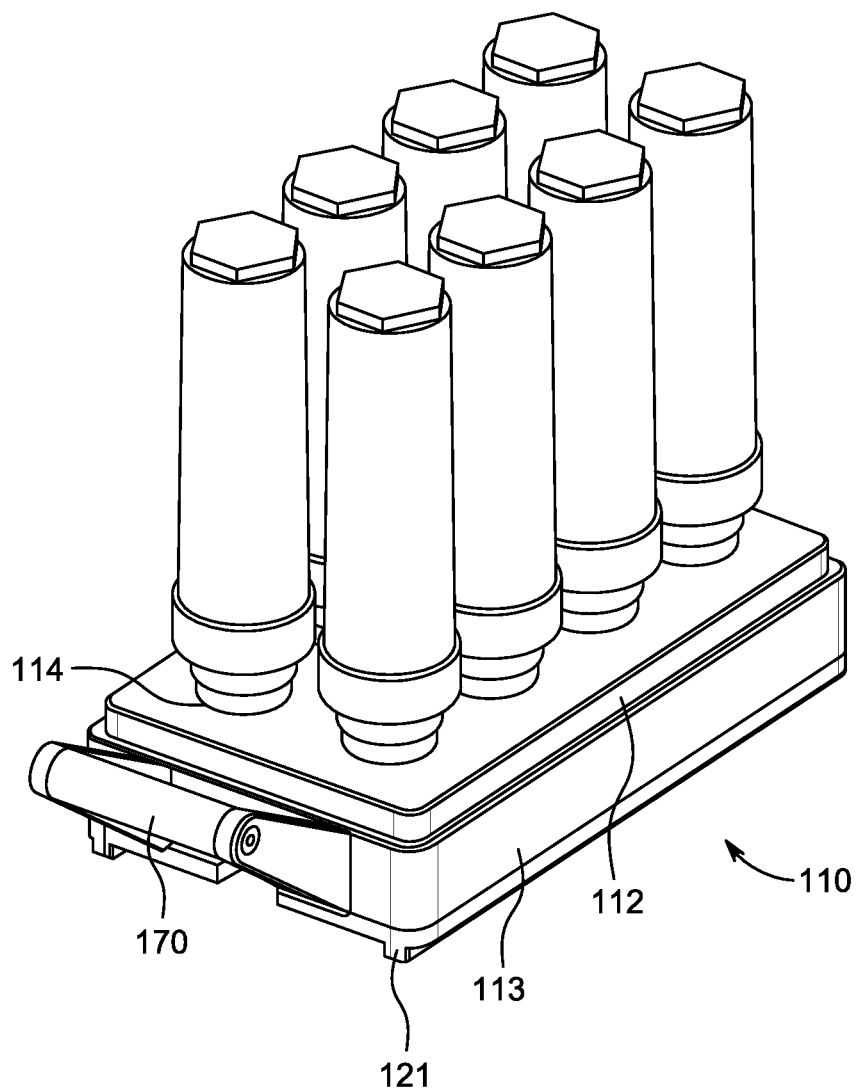
FIG. 5 illustrates an exemplary angled overall view of a platform 110 tied to the pig cleaning and transportation system 100, in accordance with one or more embodiments.

FIG. 4 illustrates an exemplary angled overall view of a second embodiment of the pig cleaning and transportation system 100 including a top cleaning element 150, in accordance with one or more embodiments. The top cleaning element 150, along with at least one side cleaning element 120, aids in the cleaning of the pigs that are currently moving thru the system 100 on the platform 110. In the embodiment of the system 100 shown in FIG. 4, the top cleaning element 150 includes an axis 152 suspended across two side cleaning elements 120 and a cleaning material 154 along the axis 152. In this embodiment the axis 152 is suspended to allow the cleaning material 154 to rotate across the top of the plurality of pigs during the pig cleaning process. Other embodiments may include multiple top cleaning elements 150 connected with at least one side cleaning element 120 to better facilitate cleaning as the pigs pass thru the system 100. The cleaning material 154 may comprise any similar or compatible materials to that of the cleaning material 128 used within the side cleaning elements 120 within the system 100 (i.e. sponges, cloth, and/or paper products that will distribute cleaning solutions and/or compounds and clean the pigs within the system 100). In other embodiments, the top cleaning element 150 may also utilize the same elements as the side cleaning elements 120 rather than the axis/roller design presented in FIG. 4. Utilizing the same design for the cleaning elements would allow for efficiencies in building the system 100 without any possible decrease in effectively cleaning the pigs themselves. Any combination of cleaning elements may be used for the system 100 so long as the required level of cleaning and sanitation is reached for the pigs going thru the system 100.

Figure 6:
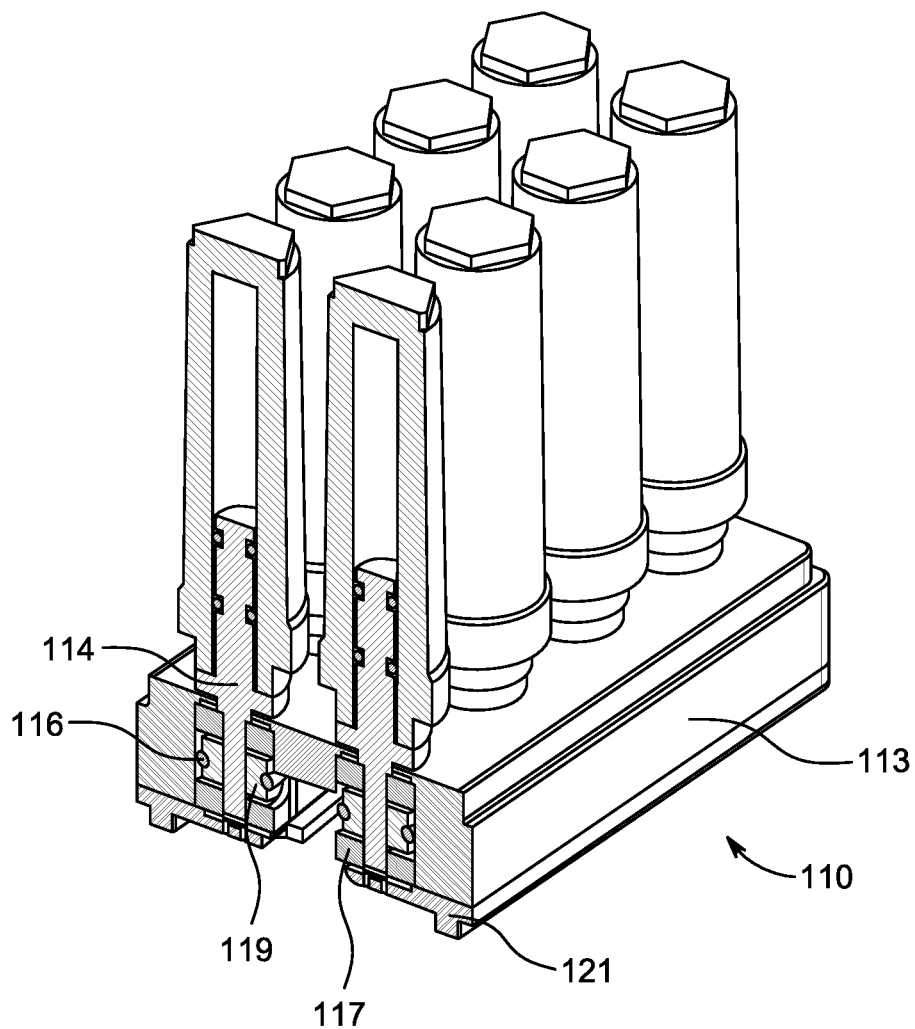
FIG. 6 illustrates an exemplary angled overall slice view of a platform 110 tied to the pig cleaning and transportation system 100, in accordance with one or more embodiments.

FIG. 6 illustrates an exemplary angled overall view of a platform 110 tied to the pig cleaning and transportation system 100, in accordance with one or more implementations. As shown in this figure the platform 110 fully separates from the rest of the system 100 in order to transport a plurality of pigs from the system 100 to any required location for their re-use. The figure also demonstrates that the platform 110 also includes the platform surface 112, a platform base 113, and longitudinal cover guides 121. The securing mechanisms 114 on the platform surface 112 are the points of contact for the pigs during the cleaning and transportation process and become part of the cleaning environment for the pigs within the system 100. The platform base 113 provides structural stability to the entire platform 110 as well as protection for any additional elements in connection with the securing mechanisms 114 (depending on the embodiment in question). The platform base 113 also serves to structurally connect the handle 170 to the rest of the platform 110. The platform base 113 may also include a plurality of openings in order to interlock with a removable handle 170 in alternate embodiments. FIG. 6 also shows the inclusion of the longitudinal cover guides 121 to the platform 110. The longitudinal cover guides 121 are fitted to interlock with the top longitudinal surface edges of the system cover 160 (discussed further in the specification) to provide stability and support when stacking platforms 110 with covers 160 on top of each other. All four elements (the platform surface 112, the platform base 113, the longitudinal guides 121, and the handle 170) may comprise one unified piece of material compatible to the pig cleaning and transportation process. Alternatively, all four elements may also comprise separate and distinct components that are structurally joined to make up the body of the platform 110.

Figure 7:
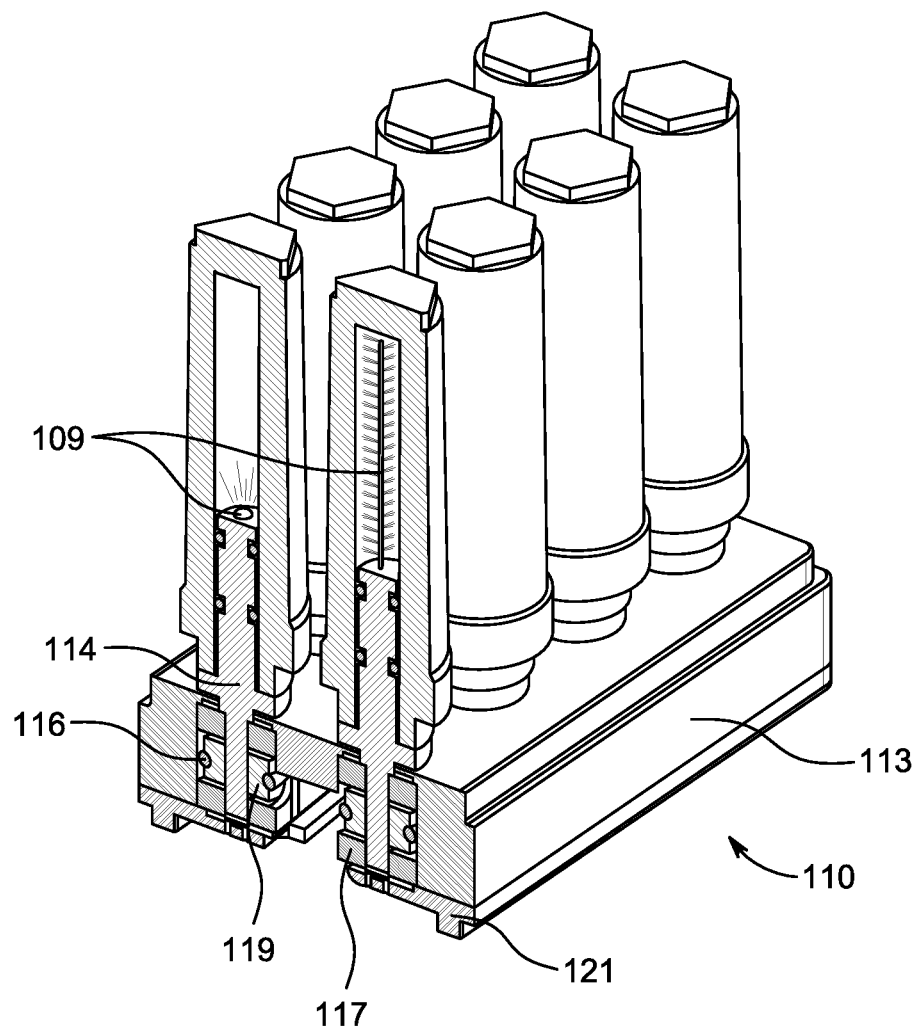
FIG. 7 illustrates an exemplary angled overall slice view of a platform 110 of the pig cleaning and transportation system 100, in accordance with one or more embodiments.

FIG. 7 illustrates an exemplary angled overall slice view of a platform 110 tied to the pig cleaning and transportation system 100. In some embodiments, each securing mechanism 114 further includes a plurality of support axes 115, each support axis 115 fitted within each aperture 111 and configured to pressure-fit the interior of a pig, each support axis 115 further including at least one O-ring 116, the O-ring 116 configured to pressure-fit between the axis 115 and the inside of the pig. This first embodiment of the securing mechanism 114 allows for the system 110 to hold each pig in place as well as to rotate each pig along its vertical axis to aid in cleaning against the cleaning material pressure surface 126. In this embodiment the support axis 115 may be sized and shaped to precisely fit the interior cavity of the pigs or may include at least one O-ring 116 in order to aid in holding the pigs in place. The thickness, hardness, and other material aspects of the at least one O-ring may vary in order to account for tolerances in cleaning multiple pigs through the system 100 over time. For example, 0-rings composed of softer rubber or rubber-like materials may be preferred to accommodate various pigs from different manufacturers during the same cleaning cycle within the system 100. Again, additional securing mechanisms 114 may be used with or without the use of O-rings 116 to provide alternative ways to secure the pigs for cleaning thru the system 100. The materials used for both the support axes 115 and the O-rings 116 may include any compatible materials that may provide the necessary support and structure during the cleaning and transportation of the pigs.

Figure 8A:
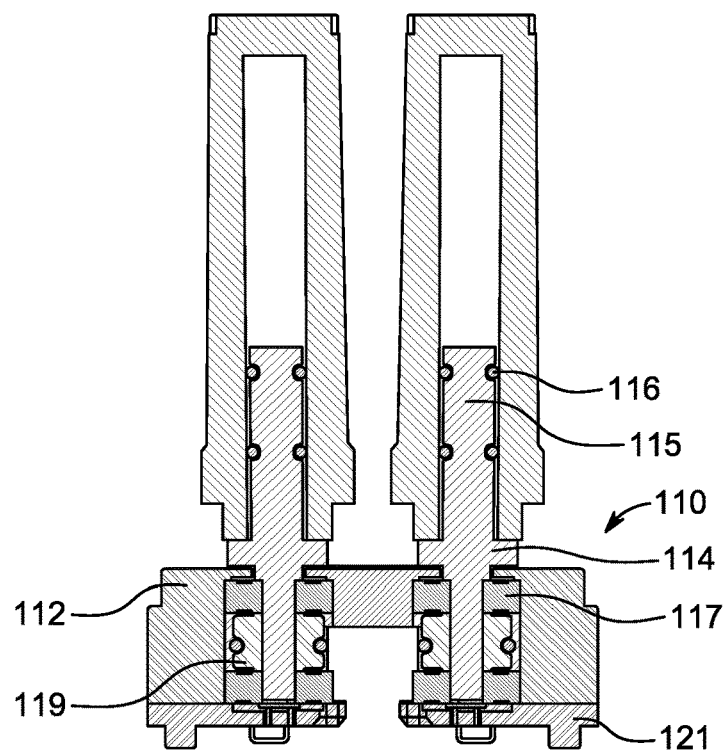
FIG. 8A illustrates an exemplary vertical axis slice view of a platform 110 of the pig cleaning and transportation system 100, in accordance with one or more embodiments.
Figure 8B:
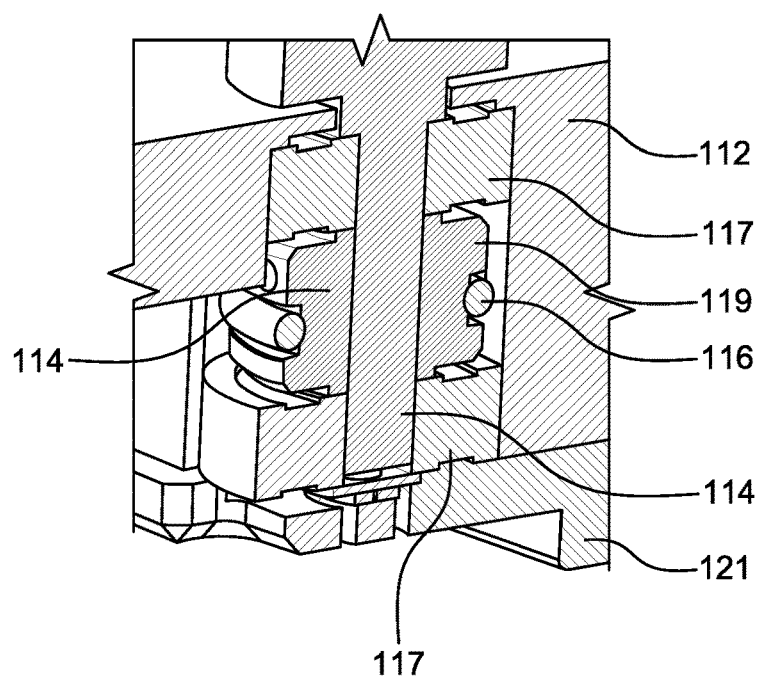
FIG. 8B illustrates an exemplary vertical angled axis slice view of a platform 110 of the pig cleaning and transportation system 100, in accordance with one or more embodiments.

FIG. 8A illustrates an exemplary vertical axis slice view of the platform 110, FIG. 8B illustrates an exemplary vertical angled axis slice view of the pig cleaning and transportation system 100, in accordance with one or more embodiments. These figures demonstrate the continued structure and included elements underneath the platform surface 112. These additional components may be structurally fixed to the securing mechanisms 114 or in sufficient structural communication to allow for functionality of the system 100. In this first embodiment, the support axes 115 continue thru an aperture 111 and is fitted into at least one bearing 117 underneath the platform surface 112. This bearing 117 provides additional support to the support axis 115 as well as frictionless rotation along the support axis' 115 vertical axis. This reduction in friction ensures that all pressure within the system 100 remains between a given pig's outer surface and the cleaning material pressure surface 126, ensuring the effective cleaning of the pigs within the system 100. Alternatively, other elements may be used in order to ensure the frictionless rotation of the support axis 115 (including, but not limited to, lubricants or other low-viscosity materials) instead of a bearing 117.

In the present embodiment within FIG. 8A and FIG. 8B, the securing mechanisms 114 may also include a pulley 119 further within the platform base 113. The pulley 119 is fitted with at least one O-ring 116 and is fitted to make pressure contact with the platform alignment rail 142. The pulley 119 will allow for the consistent rotation of all support axes 115 (and thus all pigs) during the cleaning process. Other embodiments of the system 100 may omit the pulley 118 altogether and independently rotate each support axis 115 or securing mechanism 114. Such rotation may be mechanical or manual depending on the embodiment of the system 100.

Figure 9:
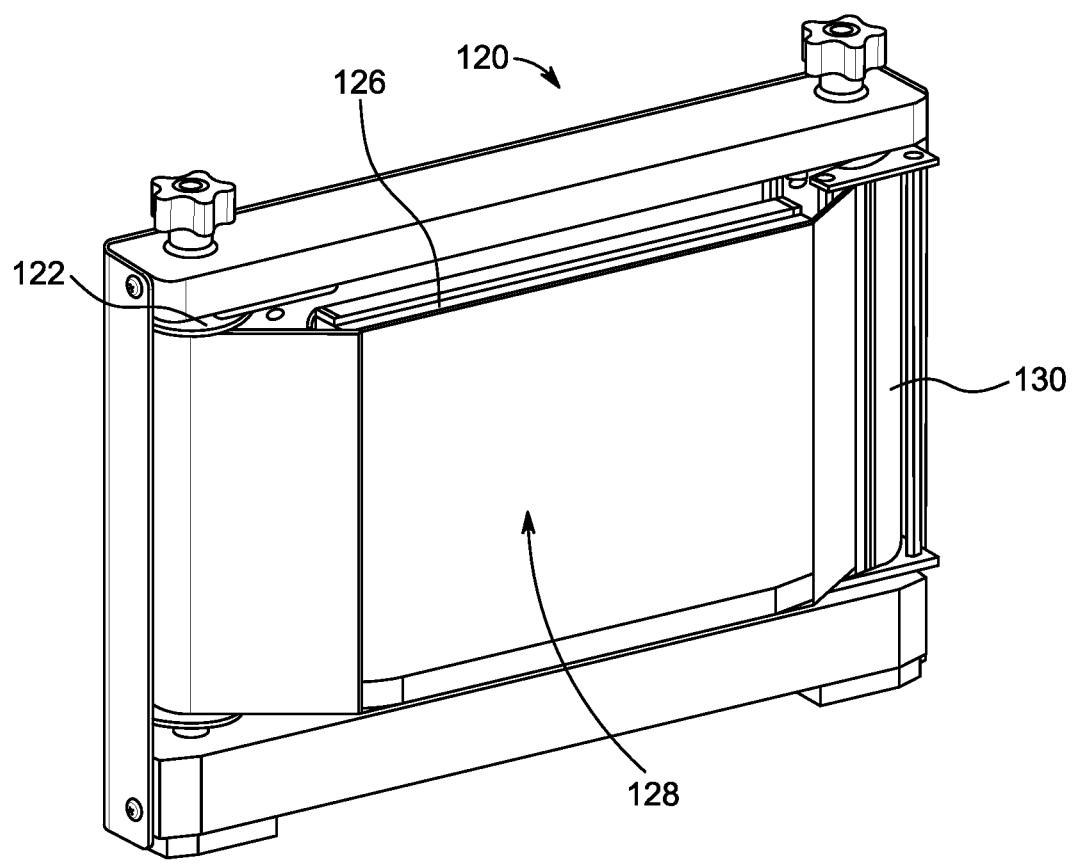
FIG. 9 illustrates an exemplary angled overall view of a side cleaning element 120 of the pig cleaning and transportation system 100, in accordance with one or more embodiments.
Figure 10:
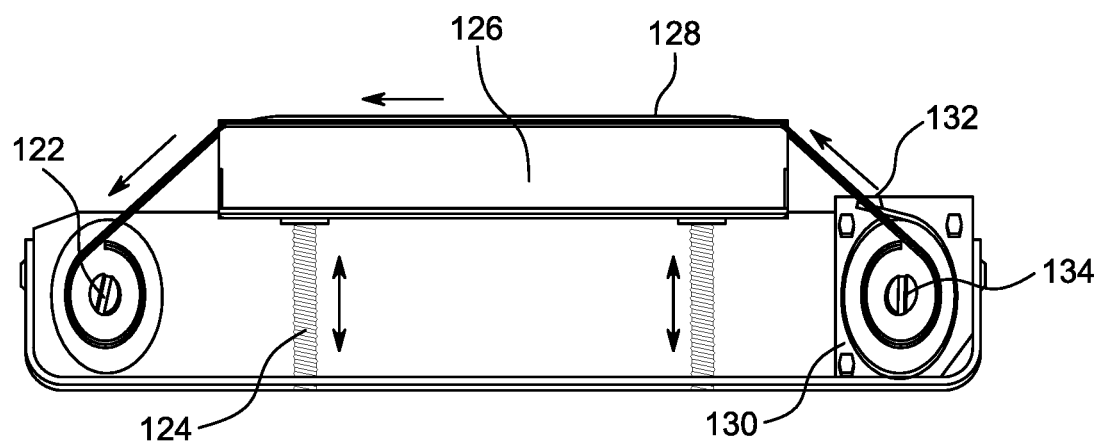
FIG. 10 illustrates an exemplary top view slice of the side cleaning element 120 of the pig cleaning and transportation system 100, in accordance with one or more embodiments.

FIG. 9 illustrates an exemplary angled overall view of a side cleaning element 120 tied to the pig cleaning and transportation system 100 while FIG. 10 illustrates an exemplary top view slice of the side cleaning element 120 tied to the pig cleaning and transportation system 100. In this first embodiment, the cleaning element 120 further includes at least one roller 122 and at least one cleaning material dispensing container 130. The at least one roller 122 and dispensing container 130 are configured to distribute a cleaning material 128 across the cleaning material pressure surface 126. As shown in FIG. 10, the cleaning material pressure surface 126 is supported by at least one spring mechanism 124. The spring mechanism 124 maintains the pressure fit between the pressure surface 126 and the plurality of pigs during the cleaning process. In this embodiment the cleaning material 128 is stored prior to use within the dispensing container 130 and may or may not contain additional sanitation solutions and/or compounds (such as alcohol, anti-bacterial gel, etc.). The cleaning material 128 is spread across the cleaning material pressure surface 126 and collected into the at least one roller 122 so that a segment of the cleaning material 128 is in pressure contact with the plurality of pigs and facilitates cleaning. The dispersion of the cleaning material 128 along with the rotation of the at least one roller 120 may be in relation to various factors, including the rotation of the pigs, the viscosity of the cleaning liquids used in combination with the cleaning material 128, the thickness and durability of the cleaning material 128, and the desired amount of cleaning material 128 in pressure contact with a given plurality of pigs within the system 100.

The cleaning material 128 may be made of paper, cloth, sponge-like plastic-based products or any material that is appropriate for the cleaning of the pigs through the system 100. Likewise, the roller 122 may also be composed of any material that will facilitate in the collection of dispersion of the cleaning material 128 during the pig cleaning process.

Other embodiments of the system 100 may include alternate combinations of rollers 122, the cleaning material dispensing containers 130, and/or cleaning materials 128 within the side cleaning element 120, depending on the cost efficiencies desired in the construction and operation of the system 100. Various embodiments may exclusively use rollers 122 with exposed cleaning material 128 during multiple cleaning processes. Another embodiment may include only one cleaning material dispensing container 130 and no roller 122 on the opposite end of the side cleaning element 120 (a possible embodiment where the cleaning material 128 is manually placed across the cleaning material pressure surface 126 during each pig cleaning process). Dual cleaning dispending material containers 130 may also be utilized in order to dispense multiple cleaning materials 128 and cleaning liquids during the pig cleaning process. Finally, in another embodiment, the side cleaning element 120 may further include a cleaning material 128 in the form of a non-moving material placed directly on or integrated into the cleaning material pressure surface 126 so that the cleaning material 128 is configured to be in static pressure contact with the plurality of pigs on the platform 110. This last embodiment would have a side cleaning element 120 without rollers 122 or dispensing containers 130. The cleaning material 128 may contain cleaning liquids depending on the requirements of the particular cleaning process within the system 100. All of these embodiments of the side cleaning element 120 may also apply to a top cleaning element 150 should the system 100 include one.

Figure 11:
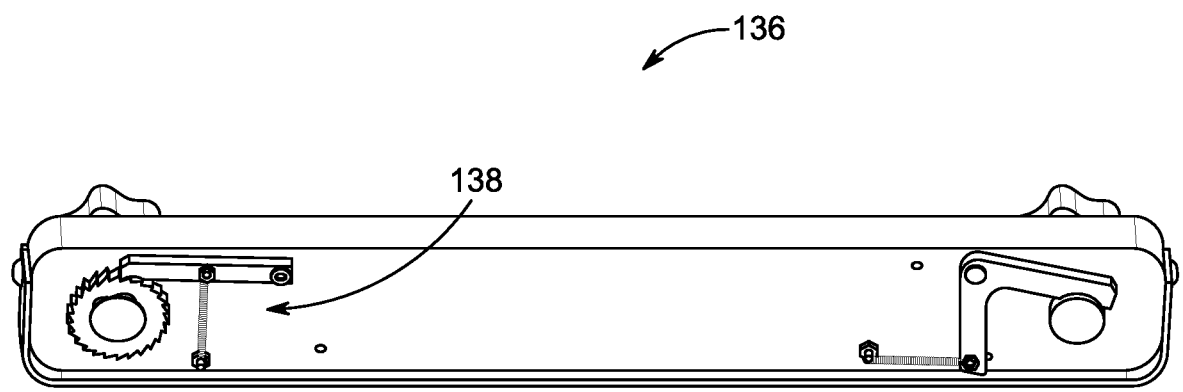
FIG. 11 illustrates an exemplary slice view of a top lid component 136 of side cleaning element 120 of the pig cleaning and transportation system 100, in accordance with one or more embodiments.

FIG. 11 illustrates an exemplary slice view of a top lid component 136 of side cleaning element 120 tied to the pig cleaning and transportation system 100. In some embodiments of the system 100 the top lid component 136 is removable in order to remove or adjust the internal components within the side cleaning element 120, including the rollers 122 or the cleaning material dispending containers 130. The top lid component 136 may also include at least one rotation mechanism 138. The rotation mechanism 138 allows for the manual or automatic rotation of a roller 122 in order to move a cleaning material 128 across the cleaning material pressure surface 126.

Figure 12:
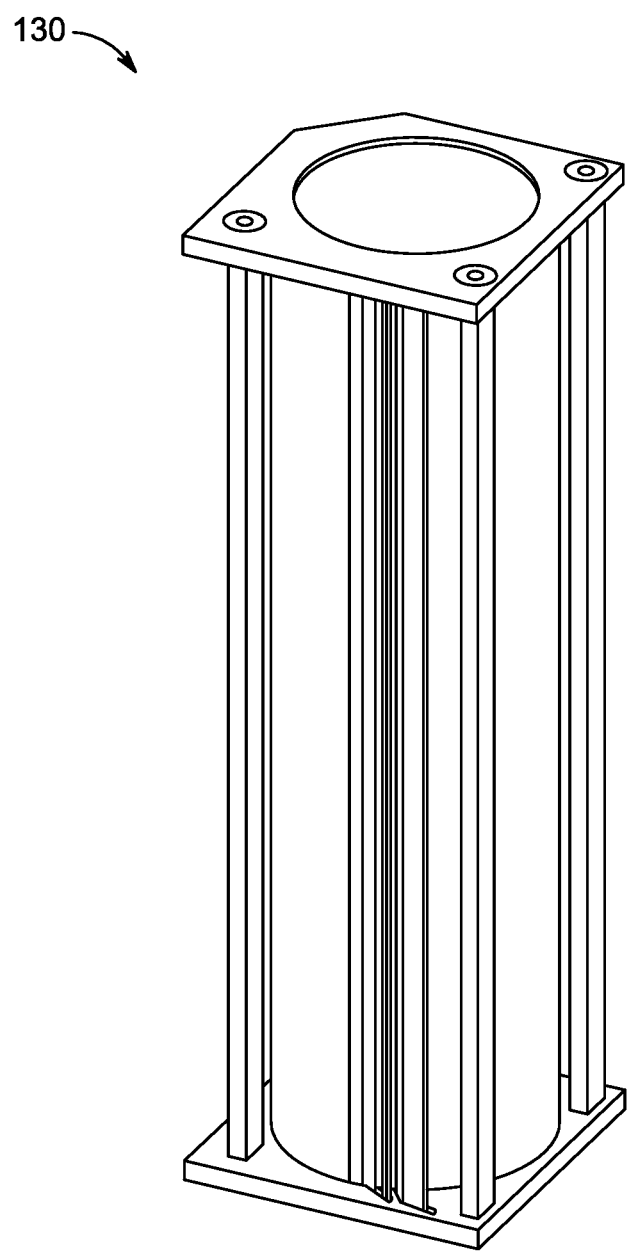
FIG. 12 illustrates an exemplary angled overall view of a cleaning material dispensing container 130 of the pig cleaning and transportation system 100, in accordance with one or more embodiments.

FIG. 12 illustrates an exemplary angled overall view of a cleaning material dispensing container 130 within the side cleaning element 120. In this figure the cleaning material dispensing container 130 includes an opening 132 configured to dispense the cleaning material 128 over the cleaning surface 126. In some embodiments the dispensing container 130 is constructed as a sealed container holding a ready to use, pre-sanitized amount of the cleaning material 128. This would allow operators of the system 100 to swap out dispensing containers 130 once all the cleaning material 128 is utilized, thus reducing any possible contamination during the cleaning process. The dispensing container 130 further includes an opening 132 which would allow for the release of the cleaning material 128 from the dispending container 130 and hold the cleaning material 128 in place across the pressure surface 126. Additionally, the dispensing container 130 may also include an internal roller 134 (shown in FIG. 10) that would support the stored cleaning material 128 as well as provide additional tension of the cleaning material 128.

Figure 13:
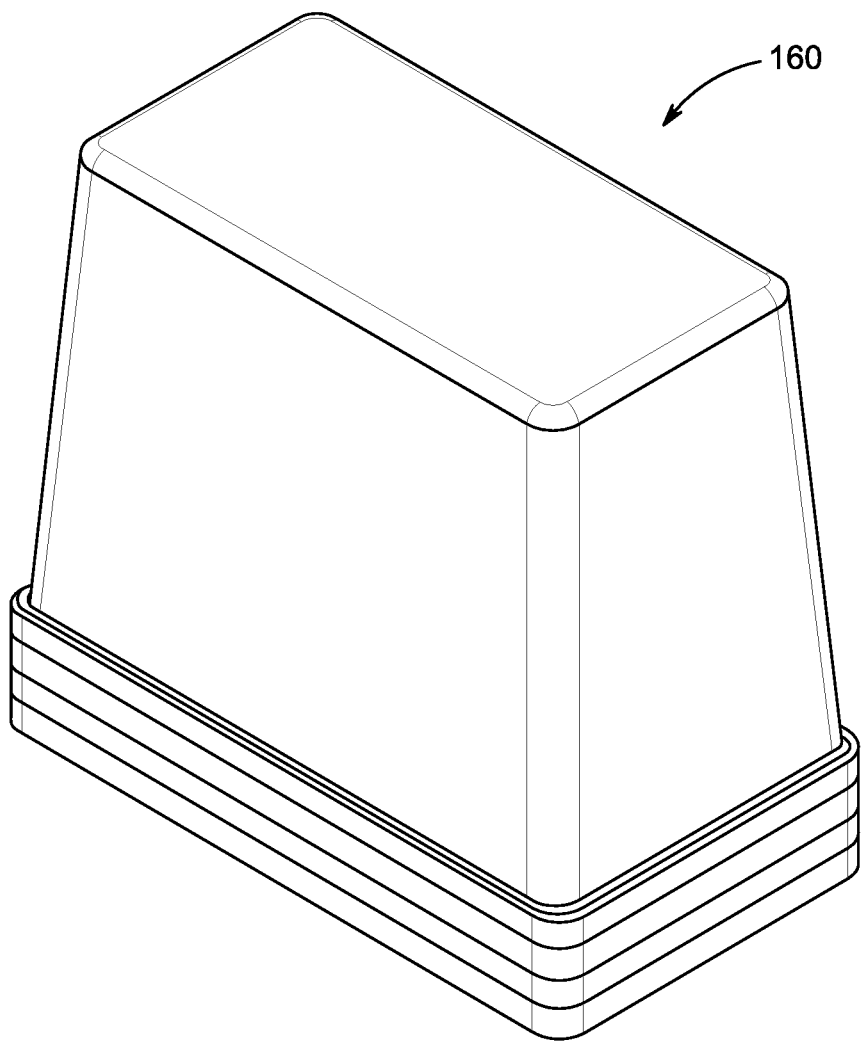
FIG. 13 illustrates an exemplary angled overall view of a cover 160 of the pig cleaning and transportation system 100, in accordance with one or more embodiments.
Figure 14:
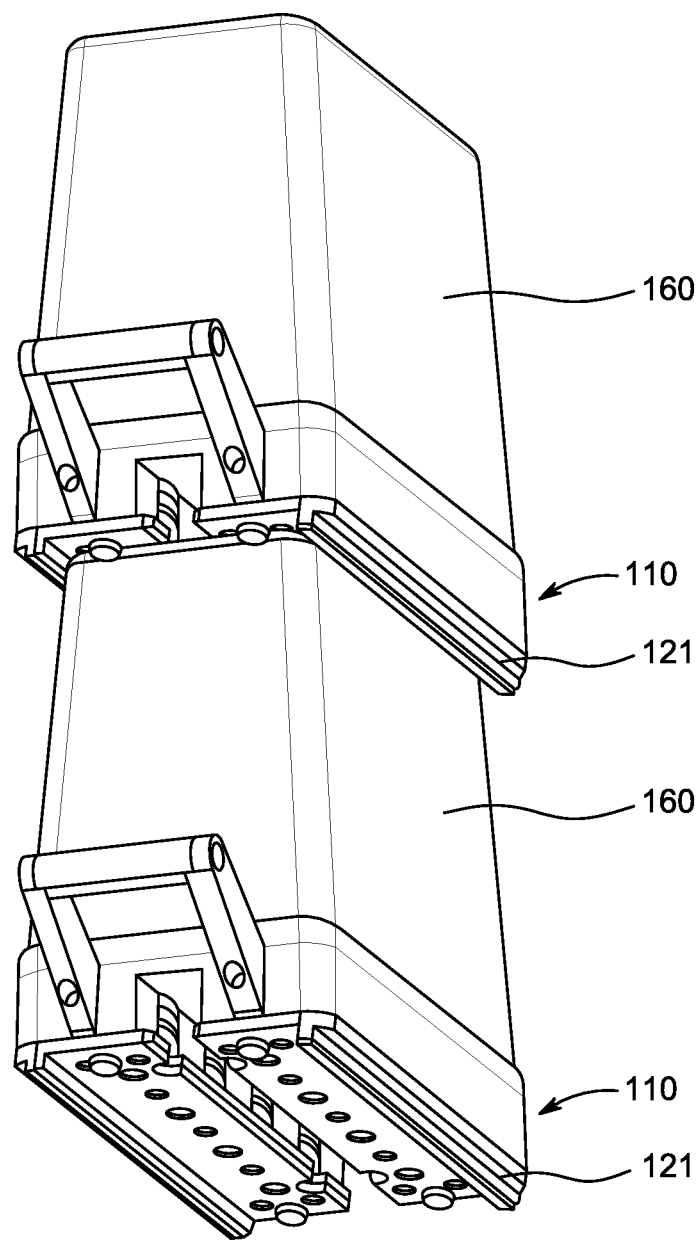
FIG. 14 illustrates an exemplary angled overall view of a plurality of platforms 110 with corresponding covers 160 and handles 170, in accordance with one or more embodiments.

FIG. 13 illustrates an exemplary angled overall view of a cover 160 tied to the pig cleaning and transportation system 100. The cover 160 is molded to fit and interlock with the platform 110 in order to keep the plurality of pigs sanitized during transport. The top of the cover 160 is also fit to interlock with bottom of the platform 110. The cover 160 is made of any corresponding material that would allow the entire surface to withstand the same sanitation materials (for example the isopropanol solution described above) as the pigs themselves. This ensures that the interior cavity of the cover 160 can maintain the same sanitized environment for the plurality of pigs within the system 100 during transport for storage and use. The cover 160 may be shaped and scaled so as to fit alongside the system 100 within a designated primary engineering control (PEC) device or room as discussed above. FIG. 14 illustrates an exemplary angled overall view of a plurality of platforms 110 with corresponding covers 160 and handles 170. As shown in FIG. 14, the top of the covers 160 are shaped to fit within the longitudinal cover guides 121 of a platform 110 resting above it. This ensure that multiple platforms 110 with covers 160 are secured when stacked on top of each other during transport.

Furthermore, the system 100 may be utilized for a method 200 of cleaning and transporting a plurality of pigs utilizing a system comprising a platform 110 with a plurality of apertures 111; a plurality of securing mechanisms 114, each securing mechanism 114 within each aperture 111 and configured to hold a pig and allow it to rotate around its longitudinal axis; a system base 140 underneath the platform 110; and a cleaning element 120 connected to the system base 140 and positioned on each longitudinal side of the platform in pressure contact with the pigs on the plurality of securing mechanisms 114, each cleaning element 120 including at least one cleaning material pressure surface 126, with the method comprising: placing at least one pig in contact with the platform 110 by way of one of the securing mechanisms 114; and moving the platform 110 along the system base 140 such that the at least one pig is rotating with the securing mechanism 114 and in pressure contact with the cleaning material pressure surface 126.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements, if any, in the claims below are intended to include any structure, material, or act for performing the function in combination with other claimed elements as specifically claimed. The description of the present invention has been presented for purposes of illustration and description but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

Although specific embodiments of the present invention have been described, it will be understood by those of skill in the art that there are other embodiments that are equivalent to the described embodiments. Accordingly, it is to be understood that the invention is not to be limited by the specific illustrated embodiments, but only by the scope of the appended claims.

Furthermore, although the present technology has been described in detail for the purpose of illustration based on what is currently considered to be the most practical and preferred implementations, it is to be understood that such detail is solely for that purpose and that the technology is not limited to the disclosed implementations, but, on the contrary, is intended to cover modifications and equivalent arrangements that are within the spirit and scope of the appended claims. For example, it is to be understood that the present technology contemplates that, to the extent possible, one or more features of any implementation can be combined with one or more features of any other implementation.

What is claimed is:

1. A pig cleaning and transportation system comprising:
   a platform with a plurality of apertures;
   a plurality of securing mechanisms, each mechanism positioned within each aperture and configured to hold a pig and allow the pig to rotate around the pig's longitudinal axis;
   a base underneath the platform; and
   a cleaning element connected to the base and positioned on each longitudinal side of the platform in pressure contact with the pigs on the plurality of securing mechanisms, each cleaning element including at least one cleaning material surface.

2. The system of claim 1, wherein the platform further includes a handle.

3. The system of claim 1, wherein each securing mechanism further includes a plurality of axes, each axis fitted within each aperture and configured to pressure-fit the interior of a pig, each axis further including at least one O-ring, the at least one O-ring configured to pressure-fit between the associated axis and an inside of the pig.

4. The system of claim 1, wherein the cleaning element further includes at least one roller and at least one cleaning material dispensing container, the at least one roller and dispensing container configured to dispense a cleaning material across the cleaning surface.

5. The system of claim 1, wherein the cleaning element further includes a sponge and at least one cleaning material dispensing container, the sponge configured to be in pressure contact with the plurality of pigs on the platform and the at least one cleaning material dispensing container configured to dispense a cleaning material onto the sponge.

6. The system of claim 1, the system further including a top cleaning element, the top cleaning element including an axis connected to at least one of the other cleaning elements of the system.

7. The system of claim 6, wherein the top cleaning element further includes:
   at least one roller, the at least one roller configured to be in pressure contact with a top of each pig of the plurality of pigs; and at least one cleaning material dispensing container, the at least one roller and dispensing container configured to dispense a cleaning material across the cleaning surface.

8. The system of claim 6, wherein the top cleaning element further includes:
   a sponge, the sponge configured to be in pressure contact with a top of each of the plurality of pigs; and
   at least one cleaning material dispensing container, the sponge and cleaning material dispensing container configured to dispense a cleaning material across the top of each of the plurality of pigs.

9. The system of claim 1, the system further including a cover configured to lock with the platform.

10. The system of claim 9, wherein a bottom of the platform is configured to fit with a top of the cover.

11. A method of cleaning and transporting a plurality of pigs utilizing a system comprising a platform with a plurality of apertures; a plurality of securing mechanisms, each mechanism within each aperture and configured to hold a pig and allows the pig to rotate around the pig's longitudinal axis; a base underneath the platform; and a cleaning element connected to the base and positioned on each longitudinal side of the platform in pressure contact with the pigs on the plurality of securing mechanisms, each cleaning element including at least one cleaning material surface, the method comprising:
   placing at least one pig in contact with the platform by way of one of the securing mechanisms; and
   moving the platform along the base such that the at least one pig is rotating with the one of the securing mechanisms and in pressure contact with the cleaning material surface.

12. The system of claim 1, wherein each securing mechanism further includes an internal cleaning mechanism, the internal cleaning mechanism configured to make contact with an interior cavity of a pig held by the securing mechanism.

13. The system of claim 12, wherein each internal cleaning mechanism further includes:
   at least one sponge, the at least one sponge configured to be in pressure contact with the interior cavity of a pig; and
   at least one cleaning material dispensing container, the at least one sponge and dispensing container configured to dispense a cleaning material within the interior cavity of the pig.

14. The system of claim 13, wherein each internal cleaning mechanism further includes a UV light element configured to emit UV light within the interior cavity of the pig held by the securing mechanism.

15. The system of claim 13, wherein each internal cleaning mechanism comprises a series a brush bristles, the brush bristles configured to make contact with the interior cavity of the pig held by the securing mechanism.

* * * * *

UNITED STATES PATENT AND TRADEMARK OFFICE
CERTIFICATE OF CORRECTION

PATENT NO. : 11,672,901 B2
APPLICATION NO. : 17/303712
DATED : June 13, 2023
INVENTOR(S) : Bretten Hug Whittacre and Jared Mark Johnson It is certified that error appears in the above-identified patent and that said Letters Patent is hereby corrected as shown below:

In the Specification

Column 1, Line 21: "the patient" should read "a patient"

Column 1, Line 27: "within" should be changed to "with"

Column 4, Line 64: "allow" should be changed to "allows"

Column 6, Line 9: Should read "decrease in the effectively effective cleaning of the"

Column 6, Line 63: Should read "one O-ring 116"

Column 6, Line 65: Replace the Numeral "0" with an "O" in the word "O-ring"

Column 7, Line 19: "is" should be replaced with "are"

Column 7, Line 38: "118" should be replaced with "119"

Column 8, Line 34: "would" should be replaced with "may"

Column 8, Line 59: "ready to use" should be replaced with "ready-to-use"

Signed and Sealed this
Third Day of September, 2024

Katherine Kelly Vidal
*Director of the United States Patent and Trademark Office*